United States Patent [19]

Mattei

[11] 4,027,676

[45] June 7, 1977

[54] COATED SUTURES

[75] Inventor: Frank V. Mattei, Piscataway, N.J.

[73] Assignee: Ethicon, Inc., Somerville, N.J.

[22] Filed: Jan. 7, 1975

[21] Appl. No.: 539,122

[52] U.S. Cl. .............................. 128/335.5; 427/2; 428/378

[51] Int. Cl.² ....................................... A61L 17/00

[58] Field of Search ...................... 128/335.5, 335; 428/262, 375, 378; 427/2

[56] References Cited

UNITED STATES PATENTS

| | | | |
|---|---|---|---|
| 2,576,576 | 11/1951 | Cresswell et al. | 128/335.5 |
| 2,734,506 | 2/1956 | Nichols et al. | 128/335.5 |
| 3,413,079 | 11/1968 | Rich | 128/335.5 X |
| 3,478,140 | 11/1969 | Kronenthal et al. | 128/335.5 X |
| 3,867,190 | 2/1975 | Schmitt et al. | 128/335.5 X |
| 3,896,814 | 7/1975 | Vivien et al. | 128/335.5 |
| 3,942,532 | 3/1976 | Hunter et al. | 128/335.5 |
| 3,954,635 | 5/1976 | Cummings et al. | 260/78.3 R X |

Primary Examiner—Dalton L. Truluck
Attorney, Agent, or Firm—Wayne R. Eberhardt

[57] ABSTRACT

A coated, absorbable suture wherein a particular absorbable composition comprising a film-forming polymer, a lubricant and a hydrophobic material is provided for coating sutures, particularly multifilament synthetic absorbable sutures, in order to improve the smoothness in tie-down properties of the sutures.

17 Claims, 3 Drawing Figures

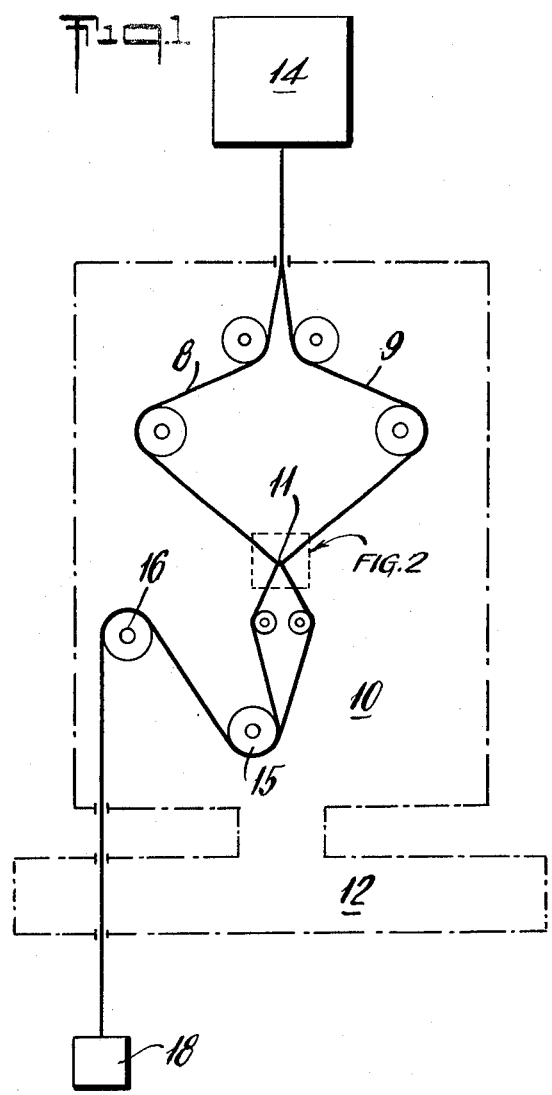
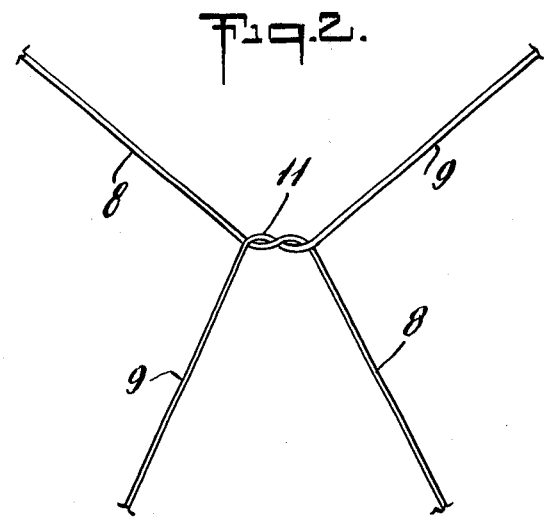
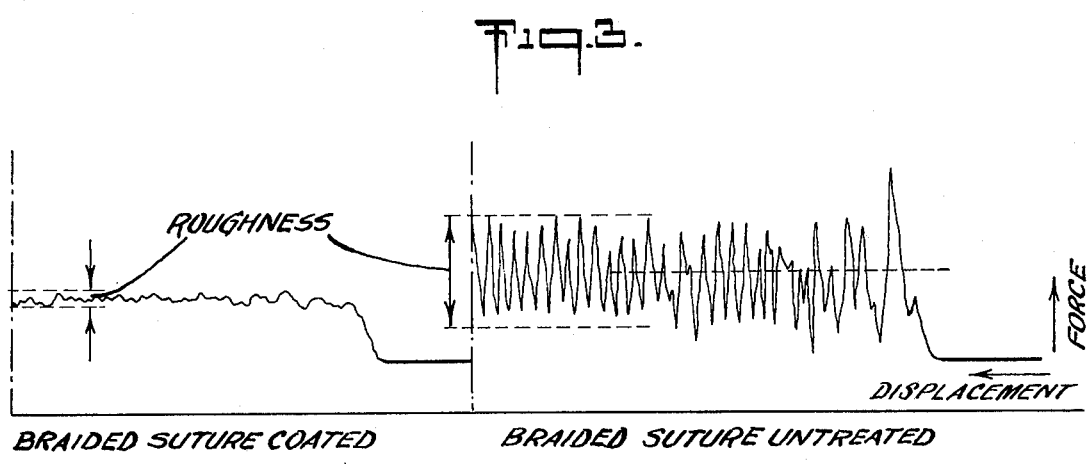

COATED SUTURES

BACKGROUND OF THE INVENTION

1. Field of Invention

This invention relates to absorbable coated suture and particularly to an absorbable composition useful as a lubricating finish for surgical sutures. More particularly, this invention relates to a means for improving the tie-down properties of synthetic absorbable multifilament sutures by coating the sutures with an absorbable composition.

2. Description of Prior Art

Suture materials are generally classified as either absorbable or non-absorbable, with each type of suture material being preferred for certain applications. Absorbable suture materials are preferred for applications in which the sewn tissues after healing will hold together without suture reinforcement and in which a non-absorbed suture may provide the possibility of an adverse bodily reaction over an extended period of time. Suture materials are considered to bb absorbable if they disappear from the sewn tisue within a year after surgery, but most absorbable suture materials preferably disappear within shorter periods.

The most commonly used absorbable suture materials are catgut and extruded collagenous materials. More recently sutures derived from synthetic polymers have been developed which are absorbable, strong, uniform and dimensionally stable, storable in the dry state and sterilizable. Typical of such polymers are lactide homopolymers and copolymers such as those disclosed in U.S. Pat. No. 3,636,956, issued to Allan K. Schneider on Jan. 25, 1972, and glycolide homopolymers such as those disclosed in U.S. Pat. No. 3,297,033, issued to Edward Emil Schmitt et al on Jan. 10, 1967, both patents being incorporated herein by reference.

Monofilament synthetic absorbable suture materials are generally stiffer than their catgut or collagen counterparts, and synthetic absorbable sutures are therefore usually employed in a braided, multifilament contruction. Such multifilament sutures exhibit a certain degree of undesirable roughness or "grabbiness" in what has been termed their "tie-down" performance, i.e., the ease or difficulty of sliding a knot down the suture into place.

Multifilament non-absorbable sutures, such as braided sutures of polyethylene terphthalate for example, can be improved with respect to tie-down performance by depositing solid particles of polytetrafluoroethylene and a binder resin on the external surface of the suture as disclosed in U.S. Pat. No. 3,527,650. This procedure, however, is undesirable as applied to absorbable sutures because polytetrafluoroethylene is nonabsorbable and sutures coated therewith would leave a residue in the sewn tissue.

Multifilament non-absorbable sutures can also be improved with respect to tie-down performance by coating them with a linear polyester having a molecular weight between about 1,000 and about 15,000 and at least two carbon atoms between the ester linkages in the polymer chain as disclosed in copending and coassigned U.S. patent application Ser. No. 303,588, now abandoned. Said application discloses that the aforementioned polyesters may also be used to coat absorbable synthetic sutures but does not consider that such coated sutures would not be totally absorbable.

The aforementioned U.S. Pat. No. 3,297,033 discloses that the synthetic absorbable sutures described therein may be coated with coating materials used on conventional sutures, such as a silicone or beeswax to modify the handling or absorption rate of the sutures. These coating materials are non-adsorbable and will accordingly leave an undesirable residue in the tissue after the suture itself is absorbed.

It is accordingly an object of the present invention to provide an absorbable coating for multifilament sutures of braided, twisted or covered construction. It is a further object of this invention to provide an absorbable coating to improve the tie-down properties of such multifilament sutures. It is a yet further object of this invention to provide a wholly abosorbable coated synthetic multifilament suture having good tie-down properties.

SUMMARY OF THE INVENTION

In accordance with the instant invention, there is provided as a coating for sutures, particularly synthetic absorbable multifilament sutures, an absorbable composition providing in combination (1) an absorbable film-former, (2) an absorbable lubricant, and (3) an absorbable hydrophobic material.

The invention also provides a method for improving the tie-down characteristics of multifilament sutures which comprises applying to the external surfaces of said sutures a liquiform absorbable composition providing in combination (1) a film-former, (2) a lubricant, and (3) a hydrophobe, and thereafter solidifying said composition as a coating on the filaments of said sutures.

Liquiform compositions include compositions which are entirely a single liquid phase such as a solution of all of the components of the absorbable coating composition in a solvent or solvent system, or a single phase melt of all of the components of the composition. They also include compositions which are uniform dispersions of immiscible liquids or solids in liquids.

Each of the components of the coating compositions has its own function in the system. The lubricant provides the lubricity to enable the contacting suture surfaces to slide with respect to each other during tie-down. The film-forming polymer is a binder holding the lubricant and hydrophobe in place on the surface of the suture and resisting displacement thereof by friction during the knotting process. The hydrophobic material prevents the over-wetting of the coating when the suture is drawn through wet living tissue and the altered properties which result from such wetting. In general, three distinct materials are required to perform these functions. It is possible, however, that one or more of these functions may be performed by single compound so that the absorbable compositions of the present invention may be comprised of less than the three above identified major functional ingredients.

BRIEF DESCRIPTION OF THE DRAWINGS

The invention and the method of the testing thereof are more readily understood by reference to the drawings in which:

FIG. 1 is a diagrammatic representation of a tensile tester for determining tie-down performance and shows two braided suture strands in position for testing;

FIG. 2 is an enlarged perspective view of the single throw knot illustrated in FIG. 1; and FIG. 3 is a representation of a typical trace of an oscillographic recorder in tie-down performance tests.

DESCRIPTION OF PREFERRED EMBODIMENT

The coating compositions of the instant invention may be applied to any suture material where it is desired to improve fiber lubricity, suture tie-down characteristics, or the like. Preferred suture compositions are synthetic absorbable multifilament sutures including in particular polylactide, polyglycolide and copolymers of lactide and glycolide with each other and with other reactive monomers such as those described for example in U.S. Pat. No. 3,636,952 and U.S. Pat No. 2,683,136, which patents are herewith incorporated herein by reference. Such preferred suture compositions are sometimes referred to herein as simply homopolymers and copolymers of lactide and glycolide.

In a preferred embodiment of the present invention, the coating is applied to the suture surfaces as a liquiform coating composition which is thereafter solidified. The liquiform composition generally comprises a solution of a film former, a lubricant and a hydrophobe in a volatile solvent, and solidification is accomplished by volatilizing the solvent. In those instances in which the solvent in the coating composition is a non-solvent or substantially a non-solvent for the suture substrate, the coating will be deposited as a distinct layer with a sharp interface between it and the substrate. in those instances in which the solvent in the coating composition is a partial solvent for the suture substrate, the solvent will soften or swell the substrate before being dried off and there will be in the final product a more gradual transition between the composition of the substrate and the composition of the coating.

The coating solution may be applied to the suture by any suitable process such as moving the suture through a receptacle containing the solution, or past a brush or applicator wetted with the solution, or past one or more spray nozzles dispensing the solution as droplets.

In place of a coating solution, the liquiform coating composition may comprise a combined melt of the constituents thereof, and in this case solidification takes place by cooling. The melt should, of course, be at a temperature below the melting temperature of the suture material, and this embodiment of the invention can be used only when the composition melts at relatively low temperatures.

The coating composition may also be a suspension or dispersion of particles of one or more of the three final coating constituents in water or in a volatile organic solvent with the other coating constituents (if any) being in solution.

In a place of a liquiform coating composition, the composition may comprise a solid which is applied to the suture by passing the suture over or between solid blocks of the coating composition which is transferred to the surface of the suture by a rubbing action.

In coating multifilament sutures with the compositions of this invention, it is not necessary that every filament within the suture be individually or completely coated. In most instances, however, the coating composition will penetrate into the suture structure, particularly when the coating composition is applied as a liquiform composition.

Suitable film formers in the coating compositions used in this invention include homopolymers and copolymers of lactide and glycolide, i.e., polylactide, polyglycolide, and copolymers of lactide and glycolide with each other and with other reactive monomers; copolymers of vinyl acetate with unsaturated carboxylic acids such as crotonic, acrylic, and methacrylic acids; water soluble or dispersible cellulose derivatives such as methyl cellulose, hydroxymethyl cellulose and carboxymethyl cellulose; natural gums; high molecular weight crystalline ethylene oxide polymers; polyacrylamide; collagen; gelatin; polyamino acids; polyvinyl alcohol; polyvinyl pyrrolidone and absorbable conjugated unsaturated triglycerides such as dehydrated castor oil.

With sutures composed of homopolymers or copolymers of lactide and glycolide, the film former in the coating composition may be a polyglycolide, polylactide or lactide-glycolide copolymer, preferably of different proportions and having different solubility characteristics than the suture. For example, a suture made of a lactide-glycolide copolymer containing about 10 percent of dilactyl moieties may be coated with a composition containing, as a film former, a lactide-gylcolide copolymer containing about 65 percent of dilactyl moieties, which copolymer is more readily soluble than the suture material in such solvents as benzene, dioxane, or 1,1,2-trichloroethane.

The film former in the coating composition may, if desired, be the same composition as the suture provided that precautions are taken to avoid dissolving the suture when the coating composition is applied. This can be done by utilizing a coating composition in which the film former is a finely divided suspension in a non-solvent liquid, or by utilizing a coating composition in which the film former is in solution at substantially saturation level and the contact time of the suture with the coating composition is short before the solvent is driven off.

Where the compositions of the suture and the film former are identical, and in other instances where the suture material may be subject to some surface dissolution and/or surface swelling or softening by reason of the action of the film former solvent thereon, there will be, as stated above, a gradual transition between the substrate composition and the coating composition rather than a sharp interface between them. There may also be some weakening of the suture accompanying the application of such coating compositions.

The lubricant of the coating composition is preferably a polyalkylene glycol having a molecular weight of less than about 200,000. Suitable polyalkylene glycols include homopolymers and copolymers of ethylene oxide and propylene oxide. Polyethylene glycol at a molecular weight from about 4,000 to about 200,000 and preferably from about 5,000 to about 50,000 is particularly preferred.

The hydrophobic material of the coating composition is preferably a higher fatty acid having more than about 12 carbon atoms such as stearic acid, or an ester of such a fatty acid such as sorbitan tristearate and hydrogenated castor oil.

The range of proportions of the coating components can vary, depending on the specific components selected and the coating properties desired. A suitable range for the proportion of film former is from about 10 to about 50 weight percent of the solidified coating; a suitable range for the proportion of hydrophobic agent is from about 10 to about 40 weight percent of the solidified coating, and a suitable range for the proportion of lubricant is from about 20 to about 60 weight percent of the solidified coating.

The proportion of liquid dispersing medium in the coating composition may also vary from zero (when the composition is applied as a solid or melt) to a level sufficient to provide a readily flowable composition but not so high as to be difficult or costly to evaporate during the formation of a solidified coating. For coating compositions which are solutions or suspensions a suitable range for the proportion of dispersing liquid is from about 70 to about 97 weight percent based on the weight of the coating composition as applied.

The coating composition may, if desired, also contain components other than those discussed above for other useful purposes including dyes, antibiotics, antiseptics, anesthetics and anti-inflammatory agents.

The amount of coating composition applied to the fiber, or the coating add-on, will vary depending upon the construction of the fiber, e.g., the number of filaments and tightness of braid or twist, and the nature of the coating material, e.g., melt, solution or solid. In general, a liquiform coating composition applied to a braid will constitute from about 5 to about 10 percent by weight of the coated fiber, but coating composition add-on may range from as little as about one percent by weight to about 15 percent or higher in some cases. As a practical matter, and for reasons of economy and general performance, it is generally preferred to apply the minimum amount of coating composition consistent with good tie-down performance, and this level of add-on is readily determined experimentally for any particular fiber-coating system.

The improvement in tie-down properties imparted to synthetic absorbable sutures may be shown qualitatively and organoleptically by comparing the feel of coated and uncoated sutures during the act of tie-down. Such comparisons are preferably made on both wet and dry sutures since many suture materials have different tie-down properties when tested wet or dry.

The improvement in tie-down properties imparted by this invention may also be shown quantitatively by a test described in the aforementioned U.S. patent application Ser. No. 303,588 and performed on equipment illustrated in FIG. 1 herein.

Quantitative tie-down measurements may be made on an instantaneous tension tester such as a Table-Model INSTRON Tensile Tester using a Type B tension cell, full-scale range 100 to 2,000 grams. The INSTRON instrument is manufactured by the Instron Corporation of Canton, Massachusetts. A high-speed SANBORN Oscillographic Recorder (Model 7702A, manufactured by Hewlett-Packard, Waltham, Massachusetts) is substituted for the standard INSTRON Recorder which would be too slow to follow the rapid changes in force that result as the sutures under test slide against each other. A high-gain DC Amplifier (Hewlett Packard Model 8803A, manufactured by Hewlett-Packard, Waltham Division, Waltham, Massachusetts) is used to interface this recorder with the INSTRON Transducer and a low-voltage DC power supply is provided to excite the transducer. The measurements are made in an air-conditioned laboratory at 72° F. and 50 percent relative humidity. To hold the specimen suture strands, a line contact jaw is used. The INSTRON machine is operated at a cross-head speed of 50 inches per minute and the chart speed of the oscillographic recorder is 20 millimeters per second.

Subjective tests for "tie-down" involve the suture configuration 11 shown in FIG. 2 (a single throw knot with each suture running over, under and over the other). The same configuration is produced by a pulley arrangement that is supported by a steel plate 10 shown in FIG. 1. The steel plate is attached to the cross-head 12 of the INSTRON tester.

To perform tie-down measurements, two strands 8 and 9 of the same suture are attached at one end to the B cell transducer 14 of an INSTRON Tester. The sutures are threaded through the pulley arrangement as shown in FIGS. 1 and 2. The other end of the suture strands are brought together, passed around the pulleys 15 and 16, and attached together to a weight 18 which provides tension on the single throw knot. A weight of 2.5 pounds is used in the standard procedure.

FIG. 3 shows typical recorder traces for a braided synthetic absorbable suture before and after coating in accordance with this invention to improve tie-down performance. The "roughness values" are measured along the ordinate and are recorded in pounds (roughness). When relatively smooth samples are compared, the amplitude of the oscillographic recorder can be increased by a factor of 20.

Roughness values for uncoated size 2-0 braided synthetic absorbable sutures in the above-described test generally range from about 5 to about 8 pounds. After coating in accordance with the instant invention the roughness values of dry sutures are usually lower than about 2 pounds and, in optimum embodiments, lower than about 1 pound. When the sutures are tested in wet condition after having been immersed in water at 25° C. for 1 minute, the roughness values of the sutures of this invention are usually lower than about 4 pounds and, in optimum embodiments lower than about 3 pounds.

EXAMPLE 1

Sixty parts by weight of a 90/10 vinyl acetate/crotonic acid copolymer, sixty parts of hydrogenated castor oil and thirty parts of solid polyethylene glycol (molecular weight about 20,000) were dissolved in 1350 parts of 1,1,2-trichloroethane, using agitation and maintaining the temperature at about 35° C. to give a 10 wt./wt.% total solids solution. Annealed size 2-0 braid made of a 10/90 mole ration L(-) lactide/glycolide copolymer and constructed of 29 yarn bundles, each containing ten filaments (three yarn bundles comprising a core and 16 carrier yarn bundles braided around the core) was led through a bath of this solution (maintained at 30°–35° C. to keep the materials in solution) over pulleys at a rate which provided about six seconds of immersion time. The braid was immediately led through a drying tower to remove most of the solvent. Drying was completed by winding the coated fiber on a spool and subjecting it to a vacuum of 100 microns for several days in a vacuum oven. The solids pick-up was found to be 7.5% based on the weight of the uncoated suture. The coated braidwas then wound on an annealing rack under mild tension and heated at 80° C. for seven minutes under nitrogen.

Using the instrumental roughness test described above, it was found that the suture had a roughness value of 0.9 lb. dry and 3.2 lbs. wet (after soaking in water for one minute). The comparable values for an uncoated suture control were 6.5 lbs. dry and 6.0 lbs. wet.

On a subjective scale of 0 to 10 (0 being roughest — comparable to the uncoated 10/90 lactide/glycolide braid and 10 being smoothest – comparable to a polyethylene terephthalate braid coated with polytetrafluoroethylene) the coated braid, in a single knot tie-down test, rated 10 in dry state and 8 in wet state.

The tensile strength of the coated braid was 10.7 lbs. under straight tension and 5.9 lbs. knotted. In the uncoated control the comparable values were 11.6 lbs. and 6.3 lbs.

Samples of coated and uncoated suture were sterilized with ethylene oxide and implanted in animals. After 21 days, the tensile strength of the coated sutures was the same as the tensile strength of the uncoated controls. After 90 days, the absorption of the coated sutures was complete and tissue reaction was at the low end of the slight reaction category.

EXAMPLE 2

Forty parts by weight of a 90/10 vinyl acetate/crotonic acid copolymer, forty parts of hydrogenated castor oil, and twenty parts of solid polyethylene glycol (molecular weight about 20,000) were dissolved in 900 parts of 1,1,2-trichloroethane, using agitation and maintaining the temperature at about 35° C. to give a 10 wt./wt.% total solids solution. Unannealed size 20 braid (otherwise similar to that of Example 1) was coated with this solution and dried in a tower and then on a spool in a vacuum, as described in Example 1. The solids pick-up was 7.7%.

The coated sutures were then subjected to an additional drying step by rewinding the coated and dried braid from the spool onto annealing racks and subjecting the rewound braid to a vacuum of 100 microns for several days. The loaded racks were then transferred, with minimal exosure to air to an annealing oven and annealed under nitrogen.

Using the test methods described in Example 1, dry and wet roughness values from the instrumental tests were found to be 0.7 lbs. and 3.7 lbs., respectively, as compared to 5.8 and 5.6 lbs., respectively, for the uncoated controls.

The subjective ratings (on the 0–10 scale described above) weere 9–10 dry and 4 wet, as compared to 0 and 0, respectively, for the uncoated controls.

The tensile strengths for straight pull and knot were 10.6 lbs. and 5.7 lbs., respectively. In vivo tests by implantation in animals gave results similar to those in Example 1.

EXAMPLE 3

Twenty-eight parts by weight of a 65/35 mole ratio L(-)lactide/glycolide copolymer (inherent viscosity 3.9), twenty-eight parts of hydrogenated castor oil and fifty-six parts of solid polyethylene glycol (molecular weight about 20,000) were dissolved in 1488 parts of 1,1,2-trichloroethane, using agitation and maintaining the temperature at about 35° C. to give a 7/wt./wt.% total solids solution. Annealed size 2-0 braid, similar to that of Example 1 was passed through the solution in a manner similar to Example 1. A tendency for the solution to ride up with the emerging fiber due to the high viscosity of the solution was controlled by passing the fibers between the folds of a felt pad located at or slightly above the surface of the solution. Drying and a subsequent short exposure to heat were conducted in a manner similar to that described in Example 1, except that the heating was for 7½ minutes at 82° C. The solids pick-up was 6%.

Using the instrumental roughness test, the suture was found to have roughness values of 1.5 lbs. (dry) and 3.0 lbs. (wet). The subjective test of Example 1 gave ratings of 9–10 (dry) and 5 (wet). Tensile values for the coated sutures were 10.4 lbs. straight and 5.9 lbs. knotted as compared to values for the uncoated sutures of 11.5 lbs. and 6.4 lbs., respectively.

The coated sutures, after sterilization, were implanted in animals. Tensile loss was normal and absorption was complete in 90 days. Tissue reaction was minimal.

EXAMPLE 4

The solution and methods of Example 3 were used to coat unannealed size 2-0 braid similar to that of Example 2. Drying and annealing were carried out as described in Example 2. Instrumental roughnes values were 1.5 (dry) and 1.5 lbs. (wet). Subjective values were 4–8 (dry) and 4 (wet). Tensile strengths were 11.3 lbs. straight and 6.2 lbs. knotted, as compared to 11.2 lbs. straight and 6.3 lbs. knotted for the uncoated suture.

Implantation of sterilized samples into animals led to absorption profiles similar to those of Examples 1 to 3.

While the foregoing specification and examples have been directed to coating absorbable multifilament sutures, it will be readily appreciated that the coating may likewise be used with good results on absorbable monofilament sutures as well as on non-absorbable monofilament and multifilament sutures.

As previously stated, catgut and collagen are among the most popular absorbable monofilament sutures in use today. These sutures are normally packaged in an aqueous tubing fluid in order to maintain suture softness and flexibility. The composition of the present invention may be used as a coating on these sutures, but precautions must be taken not to package the sutures in a tubing fluid which will dissolve and remove the coating from the suture during storage. It is generally preferred that coated catgut and collagen sutures be packaged moist but with little or no free fluid present. Alternatively, tubing fluids which are non-solvents for the coating or concentrated solutions of the coating composition itself may be used in the suture packages.

Non-absorbable sutures such as cotton, linen, silk, polyester terephthalate and polyolefins are normally coated with non-absorbable compositions. Polyolefins are usually of monofilament construction while cotton, linen, silk and polyester are usually of braided, twisted or covered multifilament construction. While there is usually no requirement that the coating on such sutures be absorbable, the composition of the instant invention may, nevertheless, be used as a lubricating finish if desired.

In the above examples, the coating solution was applied to the final suture structure and a coating layer was formed on at least the outward-facing surfaces of the outer-most filaments of the braid. It is understood, however, that the coating solution may be applied, if desired, to the individual filaments before being formed into strands or to the individual strands before being formed into the final suture structure. Also, while all the above examples were conducted with size 2-0 braided suture, this was for the sake of convenience only, and invention is not limited as to suture size but may be practiced for example with sutures from size 8-0 to size 2 and larger. The foregoing examples are intended to be merely illustrative, and many modifications and variations thereof will be apparent to those skilled in the art.

What is claimed is:

1. A finished multifilament absorbable surgical suture having improved tie down properties characterized in that the surface of the suture is coated with an absorbable composition providing in combination:
   a. from about 10 to 50 percent by weight of an absorbable film forming polymer selected from the group consisting of homopolymers and copolymers of lactide and glycolide, copolymers of vinyl acetate with unsaturated carboxylic acids, water soluble or dispersible cellulose derivatives, natural gums, high molecular weight crystalline ethylene oxide polymers, polyacrylamide, polyvinyl alcohol, polyvinyl pyrrolidone, gelatin, collagen, polyamino acids, and conjugated unsaturated triglycerides,
   b. from about 20 to 60 percent by weight of an absorbable lubricant comprising a polyalkylene glycol having a molecular weight between about 5,000 and 200,000, and
   c. from about 10 to 40 percent by weight of an absorbable hydrophobic material selected from the group consisting of higher fatty acids and esters of higher fatty acids.

2. A suture of claim 1 wherein said suture is of braided construction.

3. A suture of claim 2 wherein said suture is composed of an absorbable polymer selected from the group consisting of homopolymers and copolymers of lactide and glycolide.

4. A multifilament suture of claim 3 wherein said suture in size 2-0 has a dry roughness value not higher than about 3 pounds.

5. A multifilament suture of claim 4 wherein said suture is a size 2-0 suture.

6. A multifilament suture of claim 5 wherein said suture has a wet roughness value not higher than about 4 pounds after being submerged in water at 25° C. for one minute.

7. A suture of claim 1 wherein said absorbable film-forming polymer is a copolymer of lactide and glycolide containing about 65 percent of dilactyl moieties and about 35 percent of diglycolyl moieties.

8. A suture of claim 1 wherein said absorbable film-forming polymer is a copolymer of vinyl acetate and crotonic acid containing about 10 percent of crotonic acid moieties and about 90 percent of vinyl acetate moieties.

9. A suture of claim 1 wherein said absorbable film-forming polymer is dehydrated castor oil.

10. A suture of claim 1 wherein said polyalkylene glycol is selected from the group consisting of homopolymers and copolymers of ethylene oxide and propylene oxide.

11. A suture of claim 1 wherein said polyalkylene glycol is a polyethylene glycol having a molecular weight between about 5,000 and about 50,000.

12. A suture of claim 1 wherein said higher fatty acid is stearic acid.

13. A suture of claim 1 wherein said esters of higher fatty acids are selected from the group consisting of sorbitan tristearate and hydrogenated castor oil.

14. A method for improving the tie down characteristics of an absorbable multifilament suture which comprises coating said suture with an absorbable composition providing in combination:
   a. from about 10 to 50 percent by weight of an absorbable film forming polymer selected from the group consisting of homopolymers and copolymers of lactide and glycolide, copolymers of vinly acetate with unsaturated carboxylic acids, water soluble or dispersible cellulose derivatives, natural gums, high molecular weight crystalline ethyleneoxide polymers, polyacrylamide, polyvinyl alcohol, polyvinyl pyrrolidone, gelatin. collagen, polyamino acids, and conjugated unsaturated triglycerides,
   b. from about 20 to 60 percent by weight of an absorbable lubricant comprising a polyalkylene glycol having a molecular weight between about 5,000 and 200,000 and
   c. from about 10 to 40 percent by weight of an absorbable hydrophobic material selected from the group consisting of higher fatty acids and esters of higher fatty acids.

15. The method of claim 14 wherein said suture is of a braided construction.

16. The method of claim 14 where said suture is composed of an absorbable synthetic polymer selected from the group consisting of homopolymers and copolymers of lactide and glycolide.

17. A method for improving the tie-down characteristics of a multifilament suture composed of an absorbable synthetic polymer selected from the group consisting of homopolymers and copolymers of lactide and glycolide which comprises coating said suture with an absorbable coating composition comprising (1) from about 10 to bout 50 weight percent of a copolymer of lactide and glycolide, (2) from about 20 to about 60 weight percent of a polyethylene glycol having a molecular weight between about 5,000 and about 50,000 and (3) from about 10 to about 40 weight percent of hydrogenated castor oil.

* * * * *

UNITED STATES PATENT AND TRADEMARK OFFICE
CERTIFICATE OF CORRECTION

PATENT NO. : 4,027,676
DATED : June 7, 1977
INVENTOR(S) : Frank V. Mattei

It is certified that error appears in the above-identified patent and that said Letters Patent are hereby corrected as shown below:

In Column 1, line 22, "considered to bb" should read --- considered to be ---.

In Column 1, line 23, "sewn tisue" should read --- sewn tissue ---.

In Column 1, line 42, "contruction" should read --- construction ---.

In Column 2, line 6, "non-adsorbable" should read --- non-absorbable ---.

In Column 2, line 15, "abosorbable" should read --- absorbable ---.

In Column 3, line 28, "in" should read --- In ---.

In Column 3, line 53, "In a place" should read --- In place ---.

In Column 6, line 43, "ration" should read --- ratio ---.

In Column 6, line 44, "29 yarn bundles" should read --- 19 yarn bundles ---.

In Column 7, line 22, "Unannealed size 20" should read --- Unannealed size 2-0 ---.

In Column 7, line 32, "exosure" should read --- exposure ---.

In Column 7, line 40, "weere 9-10" should read --- were 9-10 ---.

In Column 8, line 15, "were 1.5 (dry)" should read --- were 1.5 lbs. (dry) ---.

UNITED STATES PATENT AND TRADEMARK OFFICE
CERTIFICATE OF CORRECTION

PATENT NO. : 4,027,676
DATED : June 7, 1977
INVENTOR(S) : Frank V. Mattei

It is certified that error appears in the above—identified patent and that said Letters Patent are hereby corrected as shown below:

In Column 10, line 46, "10 to bout" should read --- 10 to about ---.

Signed and Sealed this

Thirteenth Day of June 1978

[SEAL]

Attest:

RUTH C. MASON
Attesting Officer

DONALD W. BANNER
Commissioner of Patents and Trademarks